United States Patent
Carrel et al.

(10) Patent No.: US 9,095,848 B2
(45) Date of Patent: Aug. 4, 2015

(54) PACKAGING FOR MEDICAL CONTAINERS

(75) Inventors: Franck Carrel, Pont de Claix (FR); Eric Dominicy, Revel (FR); Thomas Dubois, Echirolles (FR)

(73) Assignee: Becton Dickinson France, Le Pont-de-Claix (FR)

( * ) Notice: Subject to any disclaimer, the term of this patent is extended or adjusted under 35 U.S.C. 154(b) by 0 days.

(21) Appl. No.: 14/112,550

(22) PCT Filed: Apr. 20, 2012

(86) PCT No.: PCT/EP2012/057321
§ 371 (c)(1),
(2), (4) Date: Dec. 30, 2013

(87) PCT Pub. No.: WO2012/143533
PCT Pub. Date: Oct. 26, 2012

(65) Prior Publication Data
US 2014/0190861 A1    Jul. 10, 2014

(30) Foreign Application Priority Data
Apr. 21, 2011    (EP) .................................. 11305478

(51) Int. Cl.
*B01L 9/06*    (2006.01)
*A61M 5/00*    (2006.01)
(Continued)

(52) U.S. Cl.
CPC *B01L 9/06* (2013.01); *A61M 5/002* (2013.01); *A61M 5/008* (2013.01); *B65D 21/0233* (2013.01); *B65D 21/045* (2013.01); *B65D 71/0096* (2013.01); *B65D 71/70* (2013.01); *B01L 9/54* (2013.01); *B01L 2200/025* (2013.01); *B01L 2200/028* (2013.01); *B01L 2200/185* (2013.01);
(Continued)

(58) Field of Classification Search
CPC ................ B01L 2300/0809; B01L 2300/0858; B01L 9/00; B01L 9/06; B01L 9/54; B01L 9/543; B01L 9/547; B01L 2200/025; B01L 2200/028; B01L 2200/185; A61M 5/002; A61M 5/008
See application file for complete search history.

(56) References Cited

U.S. PATENT DOCUMENTS 3,498,494 A * 3/1970 Voorhees, Jr. ................. 206/501
3,589,511 A   6/1971 Britt
(Continued)

FOREIGN PATENT DOCUMENTS

DE    8707228 U1    7/1987
DE    29705636 U1    8/1998
(Continued)

*Primary Examiner* — Anthony Stashick
*Assistant Examiner* — Mollie Llewellyn
(74) *Attorney, Agent, or Firm* — The Webb Law Firm

(57) ABSTRACT

This packaging includes a grouping nest, a first tub, and a sealing cover. Lateral walls of the first tub are sloped to allow a nesting of this first tub in a second identical tub; the first tub includes recesses on the outer side of the tub forming tub and/or nest supporting pillars on the inner side of each wall, and having a tub and/or nest supporting surface opposite the bottom of the tub. The positioning of the recess forming a tub supporting pillar on one opposed lateral wall is different from the positioning of the recess forming a tub supporting pillar on the other opposed lateral wall allowing nesting of this first tub into a second identical tub in a first relative position of the first tub, while allowing the stacking of said first and second tubs one onto the other in a second relative position of the first tub.

13 Claims, 7 Drawing Sheets

(51) Int. Cl.
  *B65D 71/70* (2006.01)
  *B65D 21/04* (2006.01)
  *B65D 71/00* (2006.01)
  *B65D 21/02* (2006.01)
  *B01L 9/00* (2006.01)

(52) U.S. Cl.
  CPC .. *B01L 2300/0809* (2013.01); *B01L 2300/0858* (2013.01); *B65D 2571/00111* (2013.01)

(56) References Cited

U.S. PATENT DOCUMENTS

| | | | | |
|---|---|---|---|---|
| 3,643,812 A | * | 2/1972 | Mander et al. | 211/74 |
| 3,734,341 A | * | 5/1973 | Levenhagen | 206/507 |
| 4,139,098 A | * | 2/1979 | Mollon | 206/507 |
| 5,344,021 A | * | 9/1994 | Rose | 206/505 |
| 6,164,044 A | * | 12/2000 | Porfano et al. | 53/471 |
| 6,216,885 B1 | | 4/2001 | Guillaume | |
| 8,286,791 B2 | * | 10/2012 | Finke | 206/366 |
| 2009/0100802 A1 | | 4/2009 | Bush et al. | |
| 2013/0284632 A1 | * | 10/2013 | Carrel | 206/499 |

FOREIGN PATENT DOCUMENTS

| | | |
|---|---|---|
| EP | 0592994 A2 | 4/1994 |
| FR | 2771390 A1 | 5/1999 |

* cited by examiner

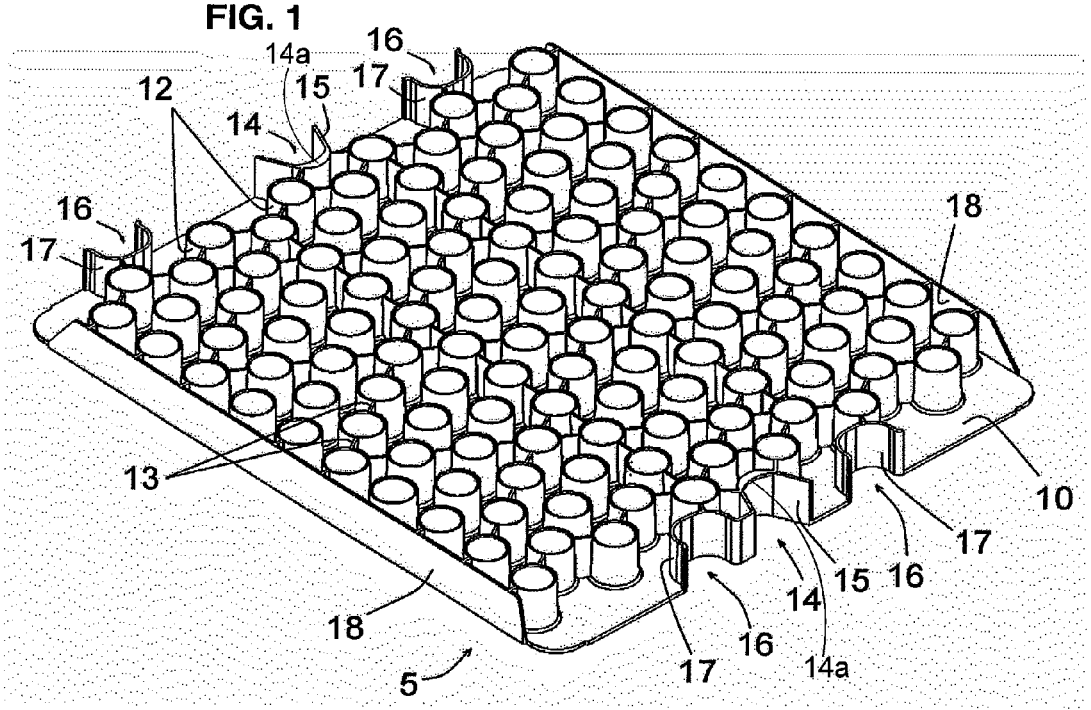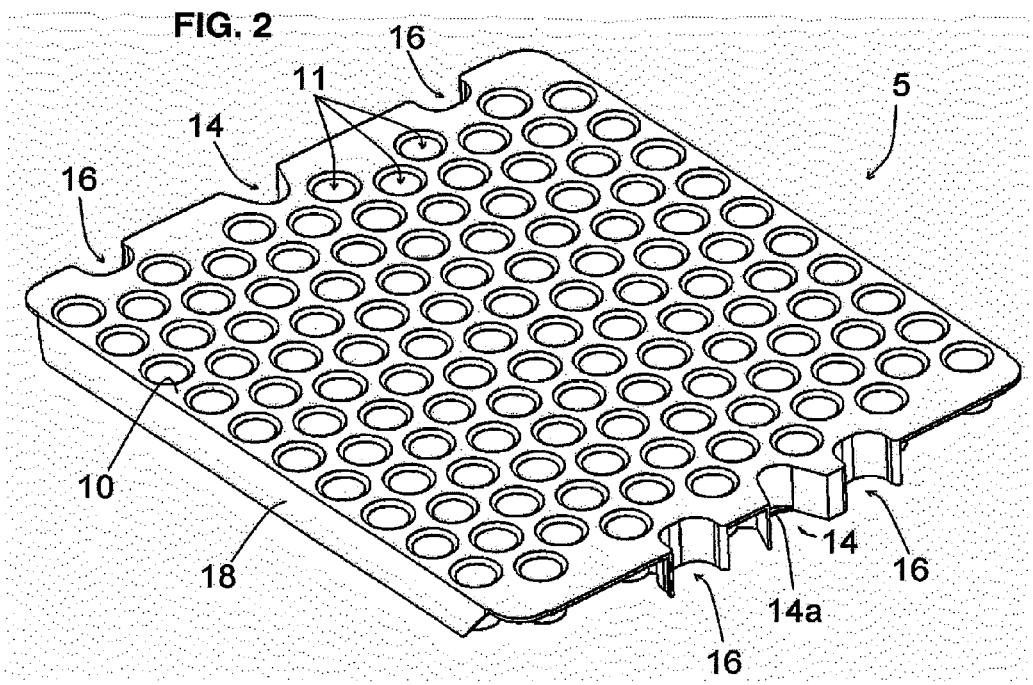

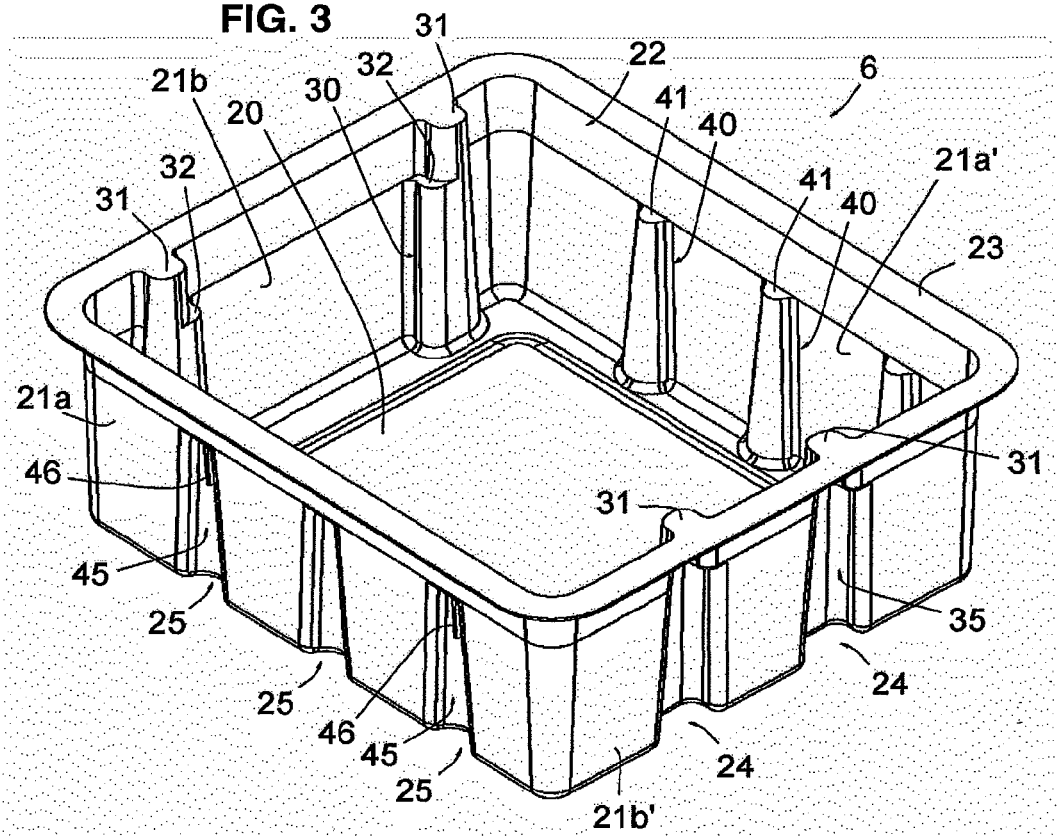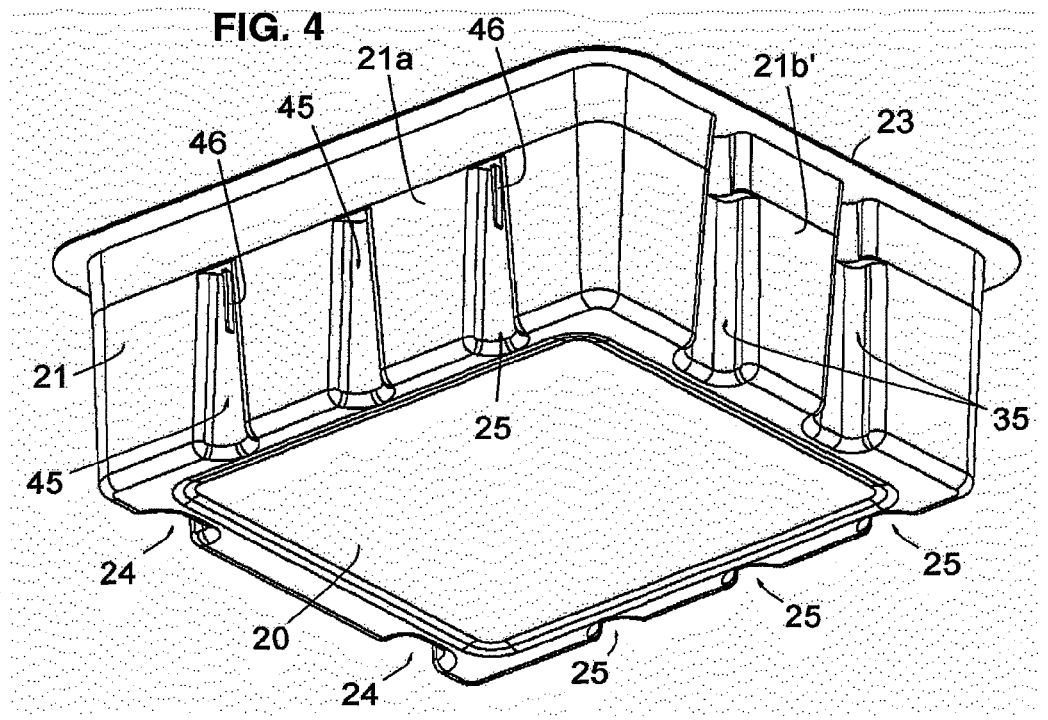

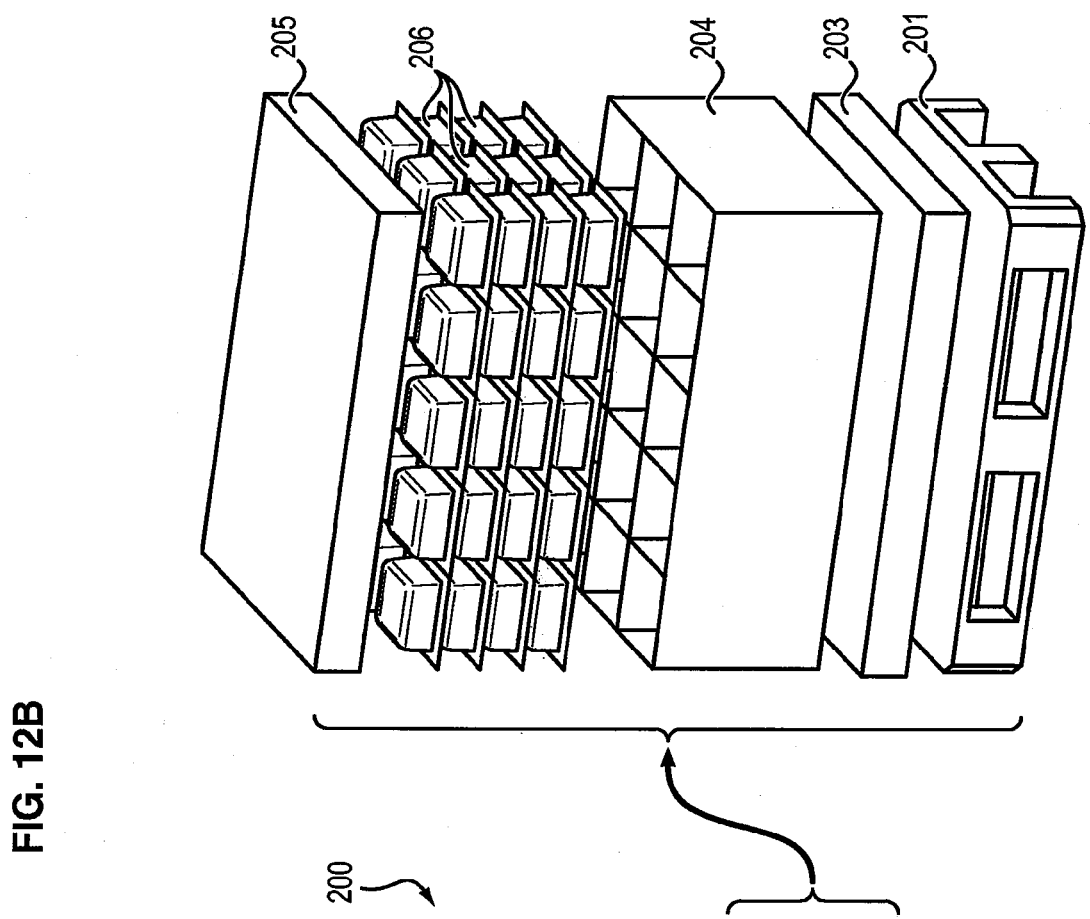
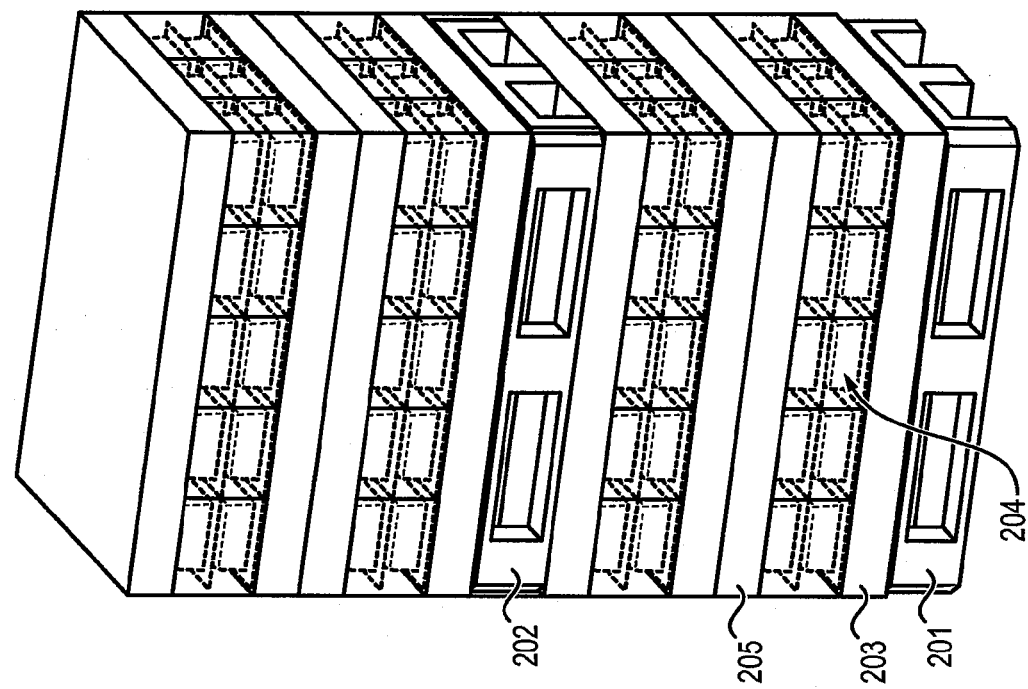
FIG. 12B

PACKAGING FOR MEDICAL CONTAINERS

BACKGROUND OF THE INVENTION

1. Field of the Invention

This invention is directed to a packaging for a plurality of medical containers such as, for example, syringes or cartridges. Each container notably comprises a cylindrical body, in particular tubular, and "upper surface" located at or near the proximal end of this cylindrical body. The flange can be integrally formed with the cylindrical body or can be a separate piece mounted on this body.

2. Description of Related Art

In the present text, the distal end of a component or of a device means the end furthest away from the hand of the user and the proximal end means the end closest to the hand of the user, when the component or device is in the use position, i.e. when the user is injecting a medicine contained in the container into his body or into another patient's body. Similarly, in this application, the terms "in the distal direction" and "distally" mean in the direction of the injection of the medicine, and the terms "in the proximal direction" and "proximally" mean in the direction opposite the direction of injection.

Often, the containers must be transported from one site to another, when they are manufactured in one site and filled in another site, or, less frequently, when they are manufactured and filled in the same site and must be delivered, once filled, to another site.

For this transportation, the containers are usually put in a packaging comprising a grouping tray or nest, hereinafter "nest", a packaging tub, hereinafter "tub", a sealing cover and a plastic bag, hereinafter "header bag" to insure the sterility. The combination of the nest, the tub, the sealing cover and the header bag will be cited hereinafter as "packaging" while the term "tub" will correspond to an empty tub.

The nest can have various shapes according to the type of containers received: it can comprise openings that can be or not coaxially surrounded by chimneys for receiving the cylindrical bodies of the containers with flanges, these flanges leaning on the upper ends of the chimneys. Alternatively, the nest can have specific openings for receiving cartridges that would be in contact with the bottom of the tub. In another embodiment, the nest can have chimneys with closed bottoms for receiving containers without flanges; the nest can also be made of a resilient material and have openings in which the containers are frictionally maintained. In the following description, the nest described is the one with openings coaxially surrounded by chimneys for receiving containers with flanges. The nest is therefore means for storing and transporting several containers at the same time without risks of contamination, breakage. Besides, this storage and transportation means can be used and re-used from the manufacture of the containers until their final filling and storage by the pharmaceutical industry.

The tub includes a peripheral outer flange levelled with its upper opening, for the sealing of the sealing cover. The tub also includes a peripheral inner flange, located below the outer flange, in order to support the nest. In use, the nest is placed into the tub which is sealed with a sealing cover, and the whole is enclosed in the header bag and sterilised. Then, series of packagings are stacked bottom up into a box, for example, a cardboard or a plastic box, with an intermediate sheet placed between two series of packagings, a series being defined as a row of several packagings.

The header bag can be a classical header bag (e.g. made of plastic including a porous part). Alternatively, the header bag can have a reinforced part positioned in such manner that the header bag gets a function of load spreader. This reinforced part can be interdependent or not with the bag, it can be in moulded or thermoformed plastic, and it can be placed inside or outside the header bag. This reinforced part can be for example at least one thermoformed plastic plate placed inside the bag below and/or above the tub. This reinforced load spreader header bag protects the containers packaged into the packaging.

When received at destination, the packagings are extracted from the box and flipped bottom down, the header bag is open, the tub is extracted from the header bag and unsealed. Then, the nests are extracted therefrom and the containers can be filled and/or handled.

The intermediate sheet placed between two series of packagings is used for distributing the load of an upper series of packagings on the lower series of packagings. Indeed, if packagings were stacked without the intermediate sheet between them to, a load would be exerted on the sealing cover of the packagings. This load could generate a contact of the sealing cover with the containers flanges, and then generate contaminating particles on the containers or lead to the breakage of the flanges.

In addition, the containers users, after removing the packagings from the box or after filling the containers, may want to store some packagings and will therefore need to stack them. This may also bring the sealing cover in contact with the containers flanges and generate contamination or breakage of the flanges in the same way.

Furthermore, this kind of packaging has the drawback of consuming a large amount of packaging materials, because only fifteen packagings can be placed in a same box (five stacked series of three packagings in width, each series being separated one from another by an intermediate sheet) and because intermediate sheets are required. For the containers users, opening many boxes and removing many intermediate sheets is burdensome and time-consuming.

The purpose of the present invention is to overcome these drawbacks. The main object of the invention is therefore to provide a packaging for medical containers which efficiently prevents from any contamination or breakage of the containers flanges when a number of packagings are stacked.

Another goal of the invention is to provide a packaging which, at the end, reduces the amount of packaging materials used for transportation and in particular that reduces the weight of the packaging.

Another goal of the invention is to provide a packaging that gives rise to an easier work for opening the box containing these packagings.

Stacking and nesting solutions for individual trays are known. The document EP0592994 discloses a cup rack consisting of a frame with a support tray located below the upper edge of the frame for carrying cups. While this cup rack can be nested and stacked, no closable packaging, such as a tub, capable to be sealed with a sealing cover is disclosed neither suggested. The document DE29705636 also discloses a support tray for receiving sensitive objects but it does not disclose any closable packaging, such as a tub, capable to be sealed with a sealing cover. Furthermore, none of these documents discloses means located into a packaging for supporting support trays. Therefore, these two documents do not provide any solution to solve the problem of containers protection against contamination from the outside.

Finally, the document U.S. Pat. No. 3,589,511 discloses a packaging with trays stacked one above the other for receiving objects. Besides, when stacked one onto another, there is a contact between objects and the upper tray. Therefore, this document does not provide any solution to protect the containers against breakage. In addition, in this document, objects are received directly within the bottom of the tray and therefore no storage and transportation means for handling several objects at the same time are disclosed.

Hence, it remains a need for a packaging solution for medical containers that would provide at the same time a simplified handling and an efficient protection of the medical containers against both contamination and breakage.

SUMMARY OF THE INVENTION

The packaging concerned comprises, in a way known per se,
- a nest comprising receiving openings for the containers,
- a tub hereinafter referred to as the "first tub", adapted to receive said nest, having:
  - a bottom wall,
  - first opposed lateral sloped walls,
  - second opposed lateral sloped walls, and
  - an upper opening with a peripheral flange,
- a sealing cover placeable on said peripheral flange to protect the containers against external contamination.

According to the invention, each of said first and second opposed lateral walls comprises at least one recess forming a supporting pillar on the inner side of said wall, with a supporting surface opposite to the bottom of the tub, and:
- a recess of each of the first opposed lateral walls forms a tub supporting pillar extending from the bottom of said tub up to the upper opening and comprising a tub supporting surface,
- a recess of each of the first and second opposed lateral walls forms a nest supporting pillar comprising a nest supporting surface extending below the tub supporting surface, and
- the positioning of the recess(es) forming a tub supporting pillar on one of the first opposed lateral walls is different from the positioning of the recess(es) forming a tub supporting pillar on the other one of the first opposed lateral walls in order to allow the nesting of this first tub into a second identical tub when empty and when the first tub is in a first relative position with respect to the second tub, while allowing the stacking of said first and second tubs one onto the other when the first tub is a second relative position with respect to the second tub, the bottom wall of the first tub being supported by the tub supporting surfaces of the second tub.

In the first relative position, the recesses of the first opposed lateral walls of said first tub are in coincidence with the tub supporting pillars of the first opposed lateral walls of said second tub for receiving the tub supporting pillars of said second tub allowing the nesting of this first tub into a second identical tub when empty.

In the second relative position, the recesses of the first opposed lateral walls of said first tub are not in coincidence with the tub supporting pillars of the first opposed lateral walls of said second tub in order to have the bottom wall of said first tub abutting the tub supporting surfaces of the tub supporting pillars of said second tub, thus allowing the stacking of the first tub on the second tub without any nesting of said first tub in said second tub and thus preventing contamination or breakage of the containers packaged into said second tub.

When inserted in the tub, the nest is supported by the nest supporting surfaces.

The nest supporting surfaces and the tub supporting pillars allow stabilizing the nest in both lateral (i.e. parallel to the bottom wall of the tub) and axial directions.

In the present text, the terms "lower" and "upper" designate something that is respectively "closer" and "farther" from the bottom of the tub or of the box in which the tubs are arranged.

The applicant has found that the problem of the contamination or breakage of the medical containers when a number of tubs are stacked is generated, with the tubs of the prior art, by an insufficient distribution of the load of upper tubs on the lower tub, this load being supported by the sealing cover. This insufficient distribution of the load also conducts to limit the number of tubs that can be stacked in a same cardboard box and requires said intermediate cardboard sheets between each layer of three tubs in order to increase, as far as possible, said distribution of said load, which results in increasing the amount of packaging materials and in said necessary work for opening the large number of cardboard boxes containing these packagings.

A tub according to the invention thus provides tub supporting pillars with tub supporting surfaces that, in said second relative position of the tubs, distribute the load of upper tubs in a stack on the lateral walls of lower tubs of this stack. In this way, the sealing covers and/or the containers of these lower tubs are free of supporting the load of upper tubs and are thus protected. As a result, much more than three tubs in height can be stacked in a cardboard box and the intermediate cardboard sheets can be omitted. In addition, the user can stack a number of packagings after removal of these packagings from the cardboard boxes without any risk of contamination or deterioration of the containers.

Additionally, the tubs, without the nests therein, can be nested one in another before putting the nests in them. This provides an advantageous space saving for the containers manufacturer, or after removal of the nests therefrom, this provides an advantageous space saving for the user of these containers.

Preferably, said first tub includes second opposed lateral walls, at least one of said second opposed lateral walls comprising at least one recessed portion forming, on the inner side of the wall, a nest supporting pillar having a nest supporting surface positioned below the tub supporting pillar and the peripheral flange of the tub, and, on the outer side of this second opposed lateral wall, a limitation recess able to slidingly receive a nest supporting pillar of said second tub when said first and second tubs are nested empty.

According to an embodiment of the invention, a recess of each of the second opposed lateral walls also forms a tub supporting pillar extending from the bottom of said tub up to the upper opening and comprising a tub supporting surface. Just like for the first opposed lateral walls, the positioning of the recess forming a tub supporting pillar on one of the second opposed lateral walls is different from the positioning of the recess forming a tub supporting pillar on the other one of the second opposed lateral walls in order to allow the nesting of this first tub into a second identical tub when empty, while allowing the stacking of said first and second tubs one onto the other, the bottom wall of the first tub being supported by the tub supporting surfaces carried by the tub supporting pillars of the first and second opposed lateral walls of the second tub.

In other words, the tub comprises at least one recessed portion on each of said second opposed lateral walls, that are identical or similar to the one of said first opposed lateral walls, i.e. each said recessed portion forming:

a tub supporting pillar with a tub supporting surface on the inner side of the second opposed lateral wall levelled with said opening, and a recess on the outer side of this second opposed lateral wall able to receive a tub supporting pillar of said second tub when nested with said first tub.

Advantageously, the packaging further comprises. a header bag that encloses the tub containing the nest and being sealed by the sealing cover.

Preferably, the tub supporting surfaces are levelled with the peripheral flange of the tub, such that when the first tub is stacked onto the second tub, the bottom wall of the first tub does not exert any pressure onto the sealing cover.

Preferably, said first tub includes limitation arrangements for limiting the depth of nesting of the first tub in said second tub when nested empty.

Said limitation arrangements can be arranged in the recess and/or in the limitation recess.

The nesting depth of a tub can thus be limited to a suitable depth allowing an easy removal of the first tub from the second tub wherein it is nested.

According to an embodiment in this case, said limitation arrangements includes a rib arranged in at least one limitation recess, said rib comprising a lower abutting end that abuts the nest supporting surface of a corresponding nest supporting pillar when said first and second tubs are nested.

According to an embodiment of the invention, the tub supporting pillars of the first and/or second lateral walls both comprise a tub supporting surface and a nest supporting surface.

Indeed, said tub supporting pillars can comprise shoulders forming nest supporting surfaces that are positioned below the tub supporting surface and the peripheral flange of the tub.

In other words, one single recess in a lateral wall forms a nest and tub supporting pillar.

In such case, the supporting pillar is generally larger than a pillar that comprises only one (nest or tub) supporting surface. Such a large supporting pillar thus improves axial and lateral stabilization of the nest and avoids the need of many pillars in the walls.

Alternatively, the nest supporting pillars are distinct from the tub supporting pillars formed on the same first and/or second opposed lateral walls.

This configuration allows a more regular distribution of the load of the nest onto the tub.

Besides, the tub is more rigid and less subject to torsion deformations.

The tub according to the invention thus provides nest supporting surfaces for receiving the nest that have limited areas, whereas the tub according to the prior art has elongated supporting surfaces for receiving the nest that form a continuous bearing shoulder on the periphery of the tub. These nest supporting surfaces of limited areas allow more space on the nest for vertically receiving syringe containers, so an increased number of syringe containers (e.g. 120 instead of 100) can be placed on a same nest in a tub having the same outer dimensions. Preferably, the nest has notches, so-called pillar notches, allowing its insertion around said supporting pillars until bearing on said nest supporting surfaces. The nest preferably has walls delimiting said pillar notches to improve the guidance of the nest when moving along the supporting pillars. Said pillar notches and corresponding walls enable the nest to be stabilized around the tub supporting pillars.

The nest has also preferably finger notches adapted for the insertion of a user's fingers for catching the nest. The nest can thus be more easily handled and transported.

Each notch can have a gripping abutment, notably a ridge, aimed at the gripping by one user's finger.

These finger notches are preferably also delimiting by walls providing increased contact surfaces for the user's fingers.

Another embodiment of the invention comprises a packaging system, e.g. a shipping unit, for transporting a plurality of packagings as described above, wherein each packaging consists of a tub containing a nest receiving a plurality of medical containers, the tub being sealed by a sealing cover placed onto the peripheral flange and closed into a header bag.

Said packaging system comprises a box wherein a plurality of packagings are stacked directly one onto the other, the tub supporting surfaces of an upper tub relying on the bottom wall of a lower tub, the tubs being stacked bottom up into the box.

BRIEF DESCRIPTION OF THE DRAWINGS

The invention will be better understood and other characteristics and advantages thereof will become evident, with reference to the attached schematic drawings, representing, by way of non-limiting and not exhaustive examples, two possible embodiments of the concerned packaging.

FIG. 1 is a perspective view of the upper part of the nest that is part of the packaging, according to a first embodiment of this packaging;

FIG. 2 is a view similar to FIG. 1, showing the lower side of this nest;

FIG. 3 is a top perspective view of a tub comprised in the packaging according to said first embodiment;

FIG. 4 is a underneath perspective view of this tub;

FIGS. 12A and 12B are comparative views of a shipping unit according to the prior art and of a shipping unit according to an embodiment of the invention, respectively.

DESCRIPTION OF THE INVENTION

Figure 5:
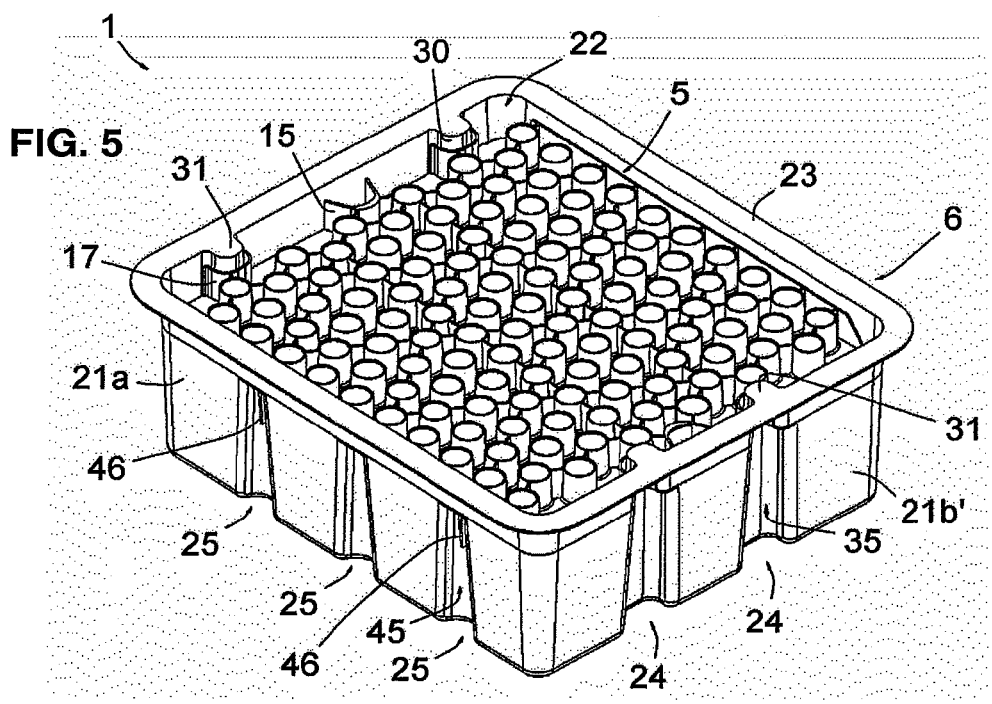
FIG. 5 is a top perspective view of the tub with the nest therein.

FIG. 5 shows a packaging 1 for the transport of syringe containers 2 (one is shown on FIG. 7), comprising a nest 5, a tub 6, and a sealing cover (not shown).

Each syringe 2 comprises a cylindrical body, in particular tubular, and a flange located at or near an end of this cylindrical body.

Referring more particularly to FIGS. 1 and 2, the nest 5 comprises a flat, substantially square or rectangular, bottom wall 10, openings 11 coaxially surrounded by chimneys 12, radial connection walls 13, median finger notches 14 on two first and second opposed edges of the bottom wall 10, walls 15 delimiting the finger notches 14, lateral positioning pillar notches 16 on said first and second opposed edges, side walls 17 delimiting the pillar notches 16, and two side walls 18 extending on third and fourth opposed edges of the bottom wall 10 that are perpendicular to said first and second edges.

Figure 7:
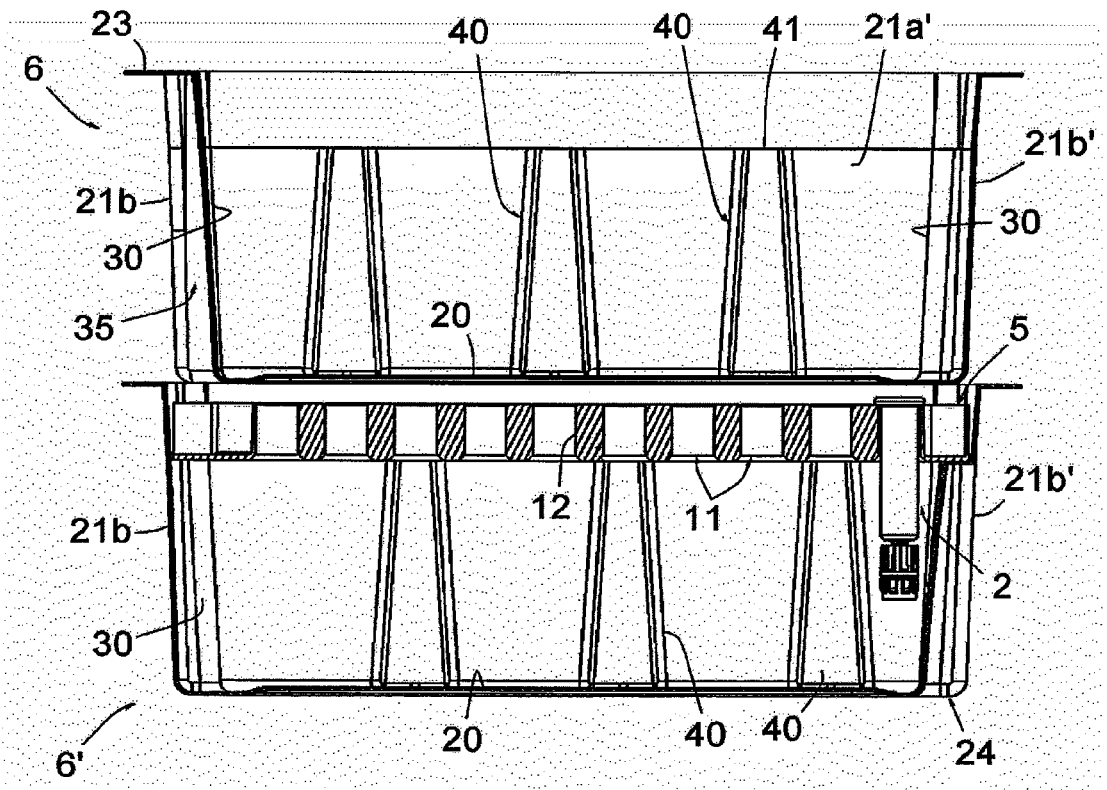
FIG. 7 is a cross-sectional view of said first and second tubs taken along the line VII-VII of FIG. 6, with a syringe placed on the nest of said second tub.

As shown on FIG. 7, the cylindrical bodies of the containers 2 are inserted in said chimneys 12 and through said openings 11 until the flanges thereof abut the upper ends of the chimneys 12.

The radial connection walls 13 connect adjacent chimneys 12 one another and connect to said side walls 18 some of the chimneys 12 that are adjacent to these side walls 18, for rigidifying the nest 5.

The finger notches 14 allow the insertion of a user's fingers therethrough, for catching the nest 5, and the delimiting walls 15 provide increased contact surfaces for these fingers. The nest 5 forms abutment ridges 14a in the finger notches 14, for improved gripping. As shown in FIGS. 1 and 2, the abutment ridges 14a may be flanges extending outwardly from the sidewall of the finger recesses 14.

The lateral positioning pillar notches 16 allow the insertion of the nest 5 on tub supporting pillars 30 of the tub 6, described below. The distance between the pillar notches 16 located on one edge is different from the distance between the pillar notches 16 located on the other opposed edge. The delimiting walls 17 improve the guidance of the nest 5 when moving along said tub supporting pillars 30.

The nest 5 is formed by a single part of moulded plastic material. With reference to FIGS. 3 and 4, the tub 6 has a bottom wall 20, first opposed lateral walls 21b, 21b', second opposed lateral walls 21a, 21a', an upper opening 22, a peripheral outer flange 23 levelled with this upper opening 22, for the sealing of the sealing cover, two recessed portions 24 in each of said first opposed lateral walls 21b, 21b', and three recessed portions 25 in each of said second opposed lateral walls 21a, 21a'.

The tub 6 is formed by a single part of moulded plastic material. The overall dimensions of the tub may be similar to the dimensions of a tub according to the prior art, thus allowing handling of the tub with the already available and existing equipments.

Each recessed portion 24 forms, on the inner side of the first walls 21b, 21b', a tub supporting pillar 30 extending and generally tapering from the bottom wall 20 up to the upper opening 22. Each tub supporting pillar 30 comprises a tub supporting surface 31 levelled with said upper opening 22 and a lower lateral shoulder 32 forming a nest supporting surface. On the outer side of the first walls 21b, 21b', each recessed portion 24 forms a recess 35 extending and generally tapering from the bottom wall 20 up to the downward surface of the peripheral flange 23.

The recessed portions 24 of the wall 21b are arranged at a same distance as the distance between two positioning pillar notches 16 of the nest 5 located on the first edge of this nest, and the recessed portions 24 of the wall 21b' opposed the wall 21b are arranged at a same distance as the distance between two positioning pillar notches 16 located on the second edge of this nest 5. The distances between the pillars 30 and recesses 35 are thus different from one wall 21b to the opposed wall 21b'.

Figure 8:
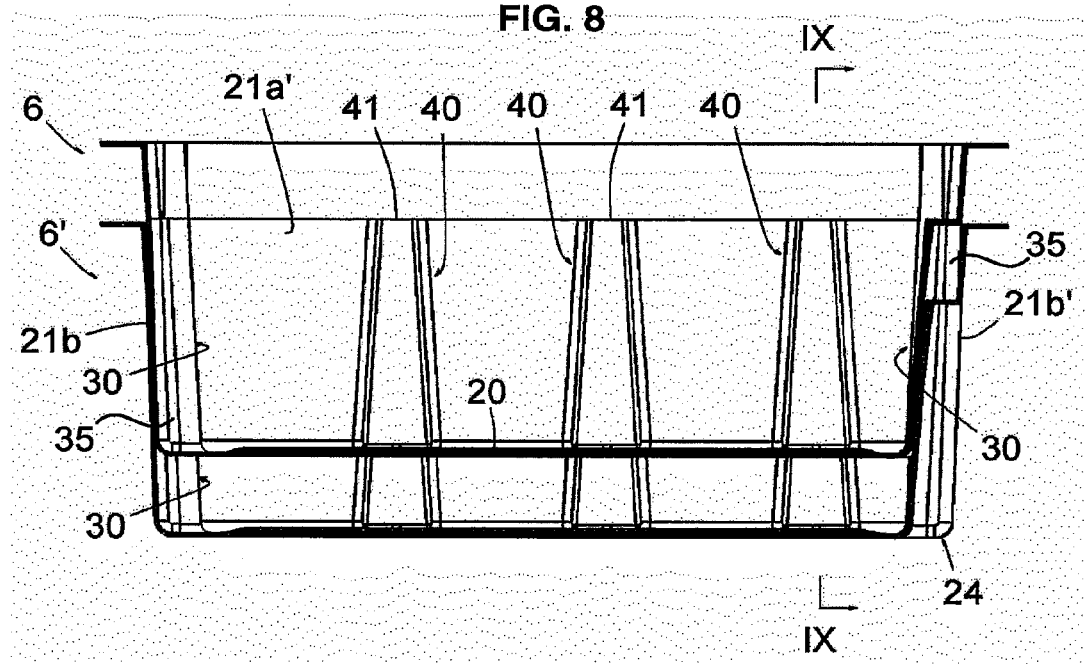
FIG. 8 is a cross-sectional view similar to FIG. 7, the upper tub having been placed in a 180° offset position with respect to the one it has on FIG. 6, and the two tubs being nested one into the other.

As shown on FIG. 8, in a first relative position of a first tub 6 above a second tub 6', wherein the recesses 35 of the first tub 6 are in coincidence with the tub supporting pillars 30 of the second tub 6' and therefore are able to slidingly receive said tub supporting pillars 30 thus allowing a nesting of said first tub 6 in said second tub 6'.

Figure 6:
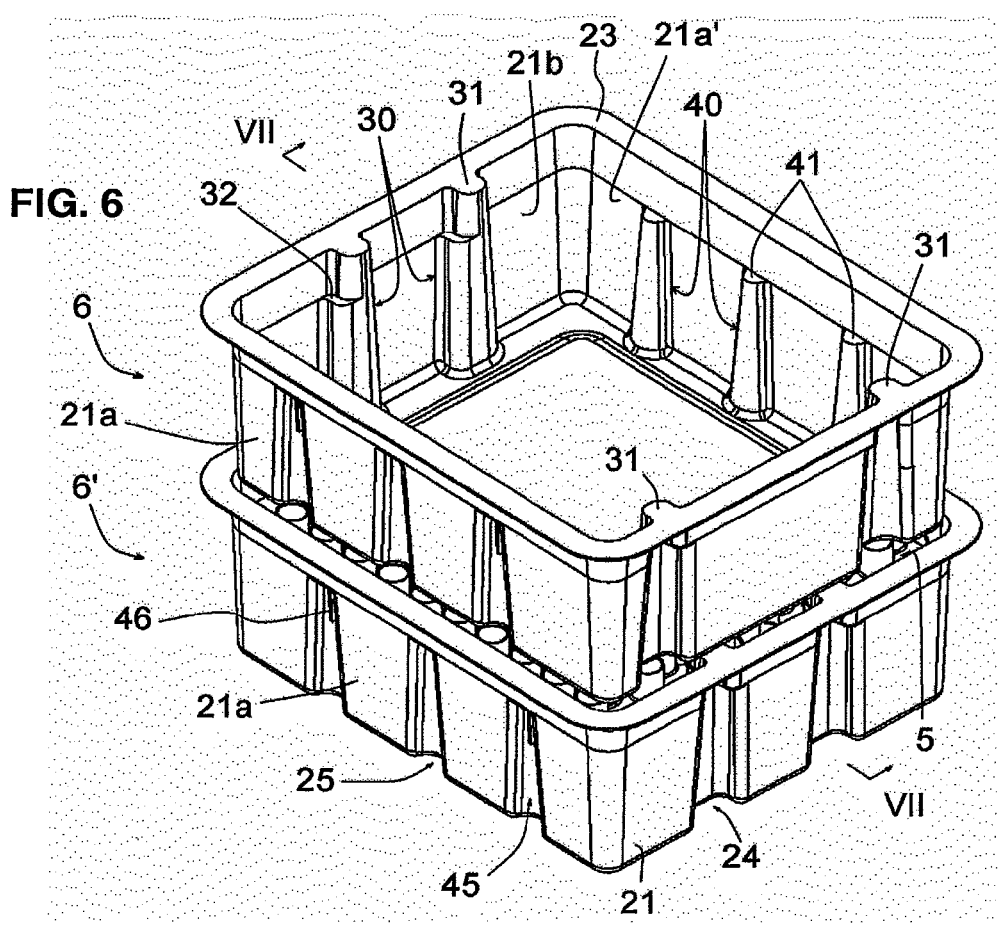
FIG. 6 is a view similar to FIG. 5, a first tub, without nest, being stacked on a second tub with a nest therein.

As shown on FIGS. 6 and 7, in a second relative position of the first tub 6 above the second tub 6', in which the tub 6 has been pivoted in a 180° offset position with respect to said first position; the recesses 35 of said first tub 6 are not in coincidence with the tub supporting pillars 30 of the second tub 6'; the bottom wall 20 of said first tub 6 thus abuts the tub supporting surfaces 31 of the tub supporting pillars 30 of said second tub 6', which allows a stacking of said first tub 6 on said second tub 6' while preventing any breakage of the medical containers.

In another embodiment (not shown), the second walls of the tub also comprise tub supporting pillars and corresponding recesses that are arranged in a similar way as for the first walls, i.e. in the above-mentioned first position, the recesses of the second walls of the first tub are in coincidence with the tub supporting pillars of the second walls of the second tub, thus allowing a nesting of the first tub in the second tub, and, in the above-mentioned second position, the recesses of the second walls of said first tub are not in coincidence with the tub supporting pillars of the second walls of the second tub, thus allowing a stacking of said first tub on said second tub.

This embodiment thus allows distributing the load of upper tubs not only onto the tub supporting pillars of the first walls but also onto the tub supporting pillars of the second walls on a lower tub.

Each recessed portion 25 forms, on the inner side of the lateral walls 21a, 21a', a nest supporting pillar 40 extending from the bottom wall 20 up to the level of said lateral shoulder 32, where it forms a nest supporting surface 41. This nest supporting pillar 40 generally tapers from this bottom wall 20 to this nest supporting surface 41. On the outer side of the walls 21a, 21a', each recessed portion 25 forms a recess 45 extending from the level of the bottom wall 20 up to the upper transverse wall forming said nest supporting surface 41, and generally tapers from this bottom wall 20 to this upper transverse wall.

Each one of the two lateral recesses 45 of each wall 21a, 21a' is a limitation recess 45 because it includes therein a median limiting rib 46 comprising a lower abutting end. As shown on FIG. 9, in said first relative position of the tubs 6, 6', each limitation recess 45 of the first tub 6 is in coincidence with a corresponding nest supporting pillar 40 of said second tub 6' below and is able to slidingly receive therein this nest supporting pillar 40 of said second tub 6', until said lower abutting end of said limiting rib 46 abuts said nest supporting surface 41. The nest supporting pillars 40 and limiting ribs 46 thus form limitation arrangements for limiting the depth of nesting of one tub 6 in the other to avoid the blocking of a tub 6 in the other tub 6'.

The sealing cover is formed by a sheet of suitable heat sealable material, in particular by a sheet in TYVEK™ (material sold by Dupont De Nemours Company), and is sealed on the outer peripheral flange 23 of the tubs 6, 6'.

The sealing cover thus closes each packaging and protects the containers arranged in this packaging from external contamination.

Figure 9:
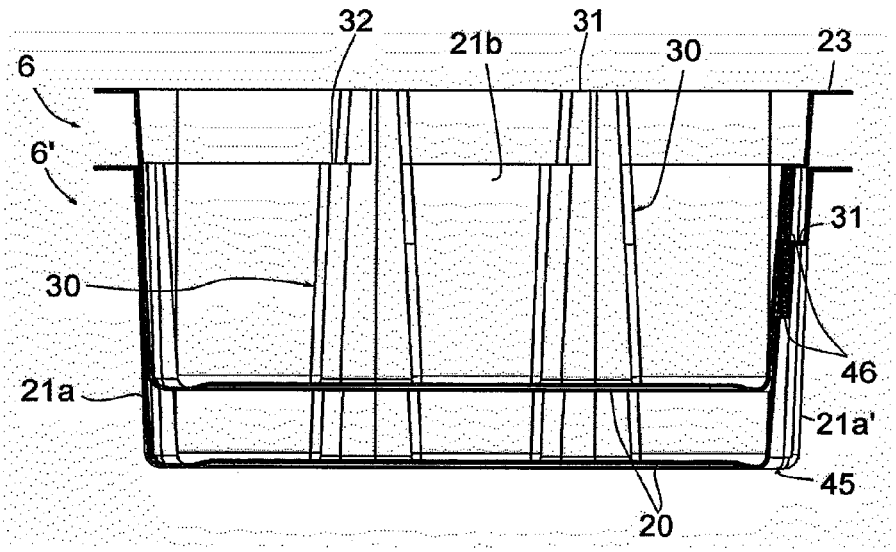
FIG. 9 is a cross-sectional view taken along line IX-IX of FIG. 8.

Before and after use, the tubs 6, 6' can be nested as shown on FIG. 9, which provides an advantageous space saving for the containers manufacturer.

After putting the nest 5 in the tubs 6, 6', placing the sealing cover on the peripheral flange and enclosing the whole in a header bag, a large number of packagings 1 can be stacked without any risk of contamination or breakage of the flanges of the containers 2, the tub supporting pillars 30, in said second relative position of the tubs 6, 6', distributing the load of upper tubs in the stack on the lateral walls of lower tubs of this stack, thus leaving the sealing covers or the flanges of the containers 2 of these lower tubs 6 free of supporting the load of the upper tubs.

In view of transporting the containers, the packaging is created as follows: containers are positioned into a nest, which is then placed into a tub where it is supported by the nest supporting pillars of said tub, then the sealing cover is sealed onto the peripheral flange of the tub.

These individual packagings are then placed into a header bag, e.g. a bag comprising a fluid-tight part and a porous part, that is sealed.

Such a header bag allows a good sterilization of the inside of the tub and prevents contamination from the outside.

Then, the individual packagings are placed bottom up in a box (e.g. made of cardboard or plastics), by simply stacking the packagings directly one onto the other, via the tub supporting pillars.

"Directly" means that no intermediate sheet is provided between two stacked packagings.

For the users of the containers 2, the packagings 1, once extracted from the transporting cardboard boxes, can be stacked temporarily, also without any risk of contamination or breakage of the flanges of the containers 2. After removal of the nests 5 therefrom, the packagings 1 also provide an advantageous space saving for this user.

Figure 10:
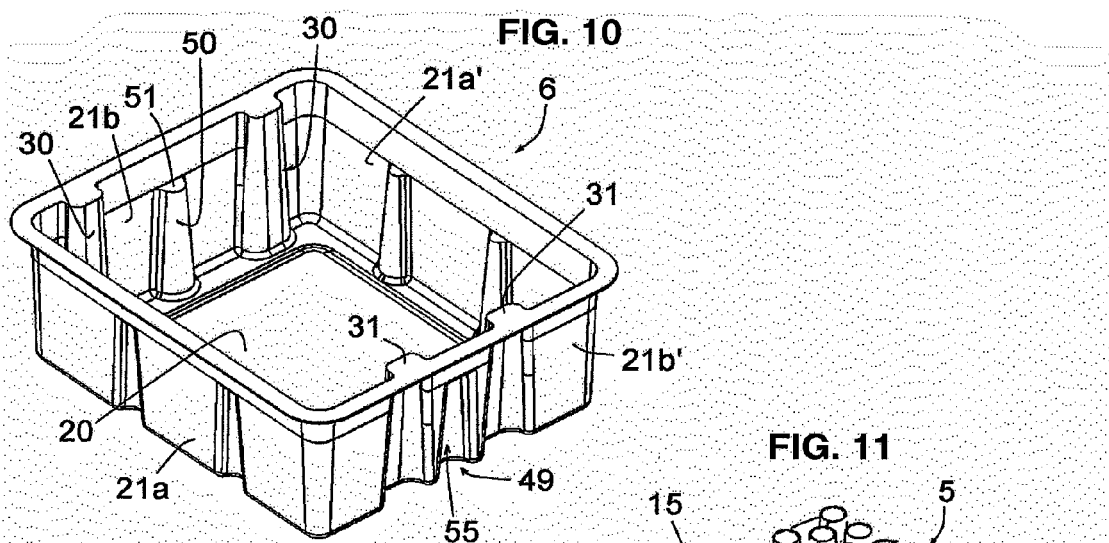
FIG. 10 is a view similar to FIG. 3 of the tub according to a second embodiment of the packaging.
Figure 11:
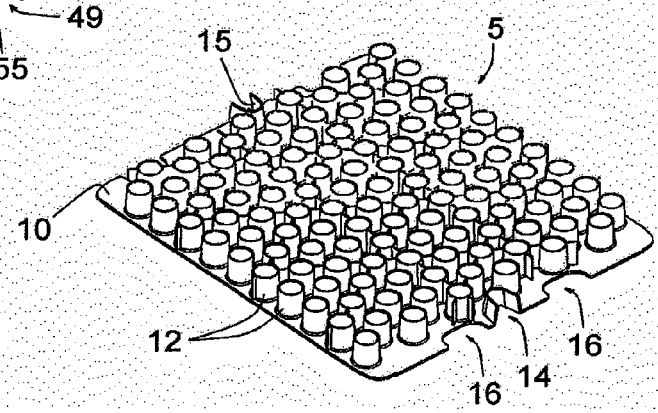
FIG. 11 is a view similar to FIG. 1 of the nest according to this second embodiment of the packaging.

In the second embodiment shown on FIGS. 10 and 11, the tub 6 comprises, median recessed portions 49 and tapered recesses 55 on the outer side of said first opposed lateral walls 21b, 21b', forming inner tapered nest supporting pillars 50 that are distinct from the tub supporting pillars 30. The upper ends of these nest supporting pillars 50 form upper nest supporting surfaces 51.

The nest 6 of this second embodiment is deprived of delimiting walls 17 and of side walls 18.

Figure 12A:
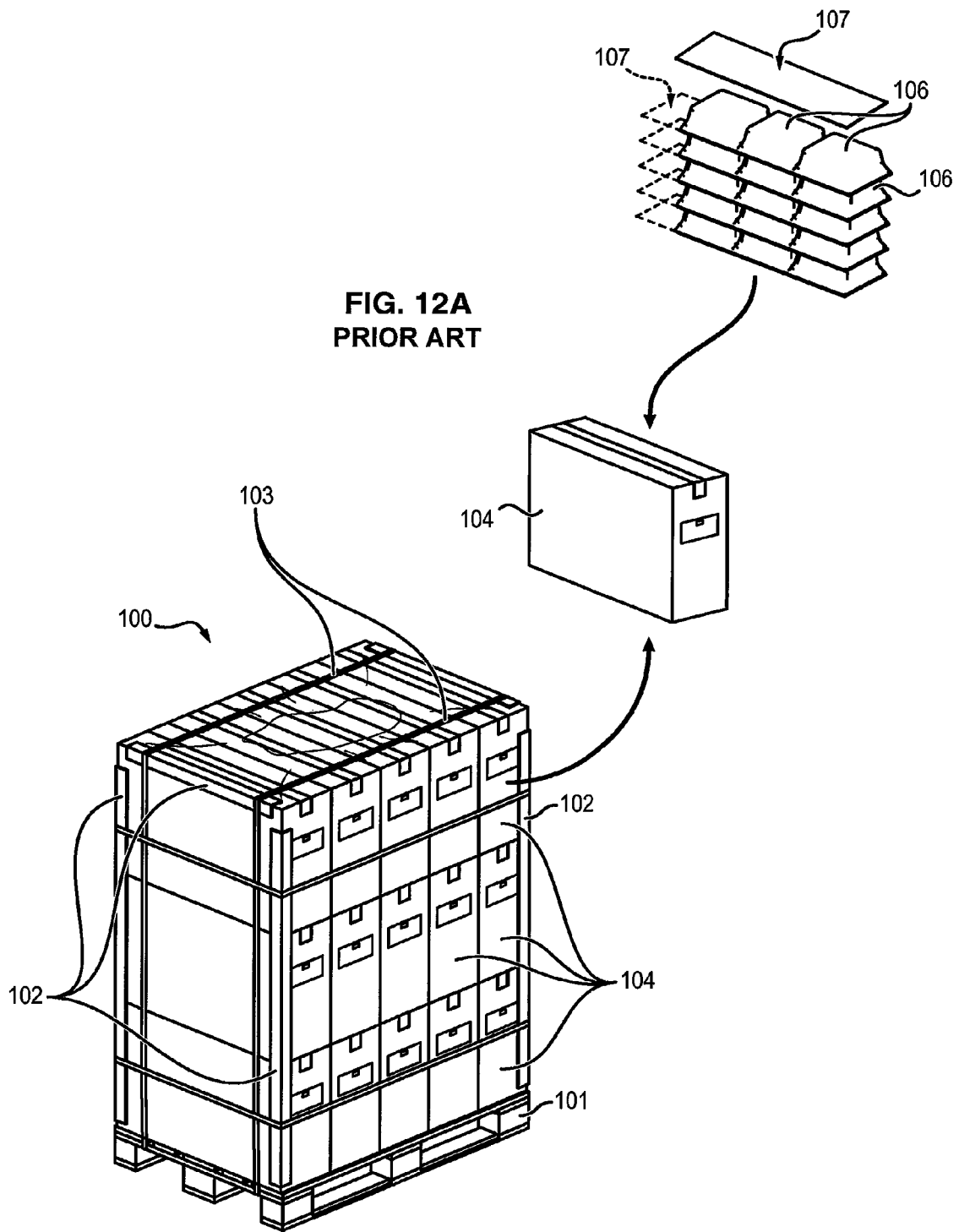

FIGS. 12A and 12B show comparative views of a shipping unit according to the prior art and of a shipping unit according to an embodiment of the invention.

As can be seen on FIG. 12A, each shipping unit 100 comprises one pallet 101 that supports three stacked rows of five boxes 104.

The boxes 104 are protected by edge protectors 102 and maintained on the pallet 101 by a tape 103.

As can be further seen on FIG. 12A, each box 104 contains five stacked rows of three packagings 106 wherein the tub is positioned bottom up.

An intermediate sheet 107 is positioned between each row of packagings 106, in order to avoid any rupture of the heat sealable material, for example a TYVEK® sheet, or fracture of the containers flanges.

Each box 104 is closed by an adhesive tape.

Each shipping unit 100 thus contains 225 packagings 106 and needs the opening of 15 boxes 104.

FIG. 12B shows a shipping unit 200 that can be formed thanks to an embodiment of the invention.

Each shipping unit 200 comprises two pallets 201, 202 that each carry two boxes 204.

Each box 204 comprises 5×3 compartments for stacks of five packagings 206 according to the invention.

Each box 204 is maintained and protected by a lower rigid tray 203 and closed by an upper rigid cover 205.

Each shipping unit 200 thus contains 300 packagings and needs the opening of only 4 boxes 204.

Besides, contrary to the shipping unit shown in FIG. 12A, no intermediate sheet is needed between two stacked packagings 206.

As it has become clear from the foregoing, the invention provides a packaging for medical containers, in particular for syringes, having, with respect to the packaging of the prior art, the determining advantages of efficiently preventing any contamination or breakage of the flanges when a number of tubs are stacked, of allowing more than three packagings to be stacked, of reducing the necessary amount of materials for transporting the packagings, and of reducing the necessary work for opening the boxes containing these packagings.

In other words, the invention does not only provide an improved arrangement of the containers in an individual packaging, but also a global packaging solution with is improved in terms of weight, ease of use and protection of the medical containers.

The invention has been described above with reference to embodiments given by way of an example. Of course, it is not limited to these embodiments and extends to all other embodiments covered by the appended claims; particularly, the invention is not limited to square or rectangular nests and tubs.

The invention claimed is:

1. Packaging for a plurality of medical containers comprising:
   a nest comprising receiving openings for the containers,
   a first tub adapted to receive said nest, having:
      a bottom wall,
      first opposed lateral sloped walls,
      second opposed lateral sloped walls, and
      an upper opening with a peripheral flange,
   a sealing cover placeable on said peripheral flange,
   wherein at least one first recess on an outer side of each of the first opposed lateral sloped walls forms, on an inner side of the respective wall, a tub supporting pillar extending from the bottom of said tub up to the upper opening and comprising a tub supporting surface,
   at least one second recess on an outer side of each of the first and second opposed lateral sloped walls forms, on an inner side of the respective wall, a nest supporting pillar comprising a nest supporting surface above a bottom of the tub extending below the tub supporting surface, and
   the positioning of the at least one first recess forming the tub supporting pillar on one of the first opposed lateral sloped walls is different from the positioning of the at least one first recess forming the tub supporting pillar on the other one of the first opposed lateral sloped walls in order to allow the nesting of this first tub into a second identical tub when empty and when the first tub is in a first relative position with respect to the second tub, while allowing the stacking of said first and second tubs one onto the other when the first tub is in a second relative position with respect to the second tub, the bottom wall of the first tub being supported by the tub supporting surfaces of the second tub.

2. The packaging of claim 1, further comprising at least one first recess on an outer side of each of the second opposed lateral sloped walls forming a tub supporting pillar on an inner side of the respective wall, extending from the bottom of said tub up to the upper opening and comprising the tub supporting surface, and the positioning of the tub supporting recess forming the tub supporting pillar on one of the second opposed lateral walls is different from the positioning of the tub supporting recess forming the tub supporting pillar on the other one of the second opposed lateral walls in order to allow the nesting of this first tub into a second identical tub when empty, while allowing the stacking of said first and second tubs one onto the other, the bottom wall of the first tub being supported by the tub supporting surfaces carried by the tub supporting pillars of the first and second opposed lateral walls of the second tub.

3. The packaging of claim 1 further comprising a header bag that encloses the tub containing the nest, the tub being sealed by the sealing cover.

4. The packaging of claim 3, wherein a first portion of the sealing cover is attached to the peripheral flange and a second portion of the sealing cover extends over the opening of the tub and the tub supporting surfaces are level with the peripheral flange, such that when the first tub is stacked onto the second tub, the bottom wall of the first tub does not exert any pressure onto the second portion of the sealing cover that extends over the opening of the tub.

5. The packaging of claim 1, wherein the nest supporting pillar comprising the nest supporting surface on each of the first opposed lateral sloped walls co-extends with the tub supporting pillar on each of the first opposed lateral sloped walls.

6. The packing of claim 1, wherein said nest supporting pillars are distinct from said tub supporting pillars.

7. The packaging of claim 1, wherein said first recesses include limitation arrangements for limiting a nesting depth of the first tub into the second tub.

8. The packaging of claim 1, wherein said nest further comprises pillar notches allowing its insertion of the nest around said tub supporting pillars such that the nest rests on said nest supporting surfaces.

9. The packaging of claim 8, wherein said nest has walls delimiting said pillar notches to improve the guidance of the nest when moving along the tub supporting pillars.

10. The packaging of claim 1, wherein said nest further comprises finger notches-adapted for the insertion of a user's fingers for catching the nest.

11. The packaging of claim 10, wherein said finger notches further comprise abutment ridges providing a better gripping surface for the user's fingers.

12. The packaging of claim 10, wherein said finger notches are delimited by walls providing contact surfaces for the user's fingers.

13. A packaging system for transporting a plurality of packagings, said packaging system comprising a box containing a plurality of packagings of claim 1, each of the packagings including the tub containing the nest with a plurality of medical containers, with the tub of each of said plurality of packagings being sealed by the sealing cover placed onto the peripheral flange and contained within a plastic bag including a porous part, the plurality of packagings stacked directly one onto the other, bottom up, such that the tub supporting surfaces of an upper tub are facing downward and are supported by the upward facing bottom wall of a downward facing lower tub.

* * * * *